United States Patent [19]

Wilkins et al.

[11] 4,335,206
[45] Jun. 15, 1982

[54] APPARATUS AND PROCESS FOR MICROBIAL DETECTION AND ENUMERATION

[75] Inventors: Judd R. Wilkins; David C. Grana, both of Hampton, Va.

[73] Assignee: The United States of America as represented by the Administrator of the National Aeronautics and Space Administration, Washington, D.C.

[21] Appl. No.: 235,796

[22] Filed: Feb. 19, 1981

[51] Int. Cl.³ ............................................. C12Q 1/04
[52] U.S. Cl. ...................................... 435/34; 435/39; 435/291; 204/195 B
[58] Field of Search ........................ 435/29, 30, 34, 39, 435/287, 291, 817; 204/195 B

[56] References Cited

U.S. PATENT DOCUMENTS

| | | | |
|---|---|---|---|
| 2,677,646 | 5/1954 | Lovell et al. | 435/297 X |
| 3,741,877 | 6/1973 | Shaufus et al. | 435/30 X |
| 3,743,581 | 7/1973 | Cady et al. | 435/291 X |
| 3,890,201 | 6/1975 | Cady | 435/34 X |
| 3,929,583 | 12/1975 | Sharpe et al. | 435/291 X |
| 4,072,578 | 2/1978 | Cady et al. | 435/291 |
| 4,149,938 | 4/1979 | Young et al. | 435/291 |
| 4,264,728 | 4/1981 | Wilkins | 435/291 X |

Primary Examiner—Robert J. Warden
Attorney, Agent, or Firm—Wallace J. Nelson; John R. Manning; Howard J. Osborn

[57] ABSTRACT

An apparatus and process for detecting and enumerating specific microorganisms from large volume samples containing small numbers of the microorganisms wherein the large volume samples are filtered through a membrane filter 23 to concentrate the microorganisms and filter 23 is positioned between two absorbent pads 21 and 25 previously moistened with a growth medium for the microorganisms. A pair of electrodes 13 and 15 are disposed against filter 23 and the pad-electrode-filter assembly retained within a petri dish 17 by retainer ring 27. Cover 29 is positioned on base 19 of petri dish 17 and sealed at the edges thereof by a parafilm seal prior to being electrically connected via connectors 14 and 16 to strip chart recorder 11 for detecting and enumerating the microorganisms collected on filter 23.

9 Claims, 3 Drawing Figures

APPARATUS AND PROCESS FOR MICROBIAL DETECTION AND ENUMERATION

ORIGIN OF THE INVENTION

The invention described herein was made by employees of the U. S. Government and may be manufactured and used by or for the Government for governmental purposes without the payment of any royalties thereon or therefor.

BACKGROUND OF THE INVENTION

The broad use of membrane filtration and electrochemical systems to detect microorganisms in various samples is well known. Membrane filtration normally requires a minimum of twenty-four hours incubation time for adequate growth to appear and requires the use of an operator to examine and count the microorganism colonies. Electrochemical detection systems presently employed have the inherent disadvantage of a high probability of missing cells when present in small numbers in large volumes and there is, at times, a long lag time to produce the required number of $10^6$ to $10^7$ cells/ml for a detectable response to occur in the system.

In the present invention an attempt is made to combine the advantageous features of both the membrane filtration and electrochemical detection systems while minimizing the disadvantages thereof.

It is therefore an object of the present invention to provide a novel apparatus and process for detecting and enumerating specific microorganisms in a sample solution.

It is another object of the present invention to combine the membrane filtration and electrochemical microbial detection systems into a simple system that may be readily employed by semiskilled operators to detect and enumerate microorganisms in a sample solution.

Another object of the present invention is a rapid process for determining water contamination of small numbers in large volumes.

Another object of the present invention is a novel apparatus for qualitatively and quantitatively detecting water sample impurities.

According to the present invention the foregoing and additional objects are attained by filtering a sample solution through a standard membrane filter impervious to the microorganism tested for, placing the membrane filter onto an absorbent pad previously moistened with a microorganism growth stimulant medium, positioning a pair of platinum electrodes on the filter surface and covering the electrodes with a second identically treated absorbent pad. This assembly is then sealed within a petri dish or like container with one exposed end of each electrode protruding from the sealed container being connected to a suitable recorder for detecting and recording the microbial growth.

BRIEF DESCRIPTION OF THE DRAWINGS

A more complete appreciation of the invention and many of the attendant advantages thereof will be readily apparent as the same becomes better understood by reference to the accompanying drawings wherein.

DETAILED DESCRIPTION OF THE INVENTION

Figure 1:
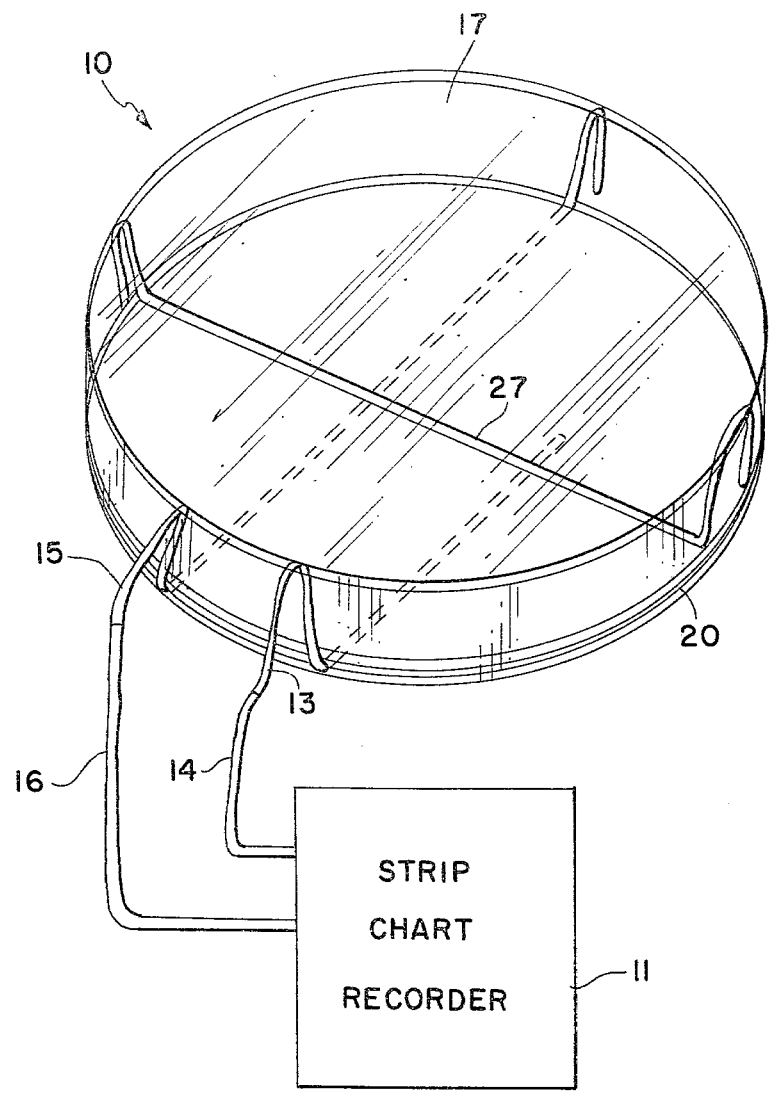
FIG. 1 is a part schematic view of a typical combined membrane-electrochemical microbial detection apparatus of the present invention.

Referring now to the drawings and more particularly to FIG. 1, the combined membrane filtration and electrochemical microbial detection system of the present invention is shown and designated generally by the reference numeral 10. System 10 includes a strip chart recorder 11 and a petri dish assembly 17. A pair of electrical leads 14 and 16 serve to connect recorder 11 to platinum electrodes 13 and 15 of dish assembly 17.

Figure 2:
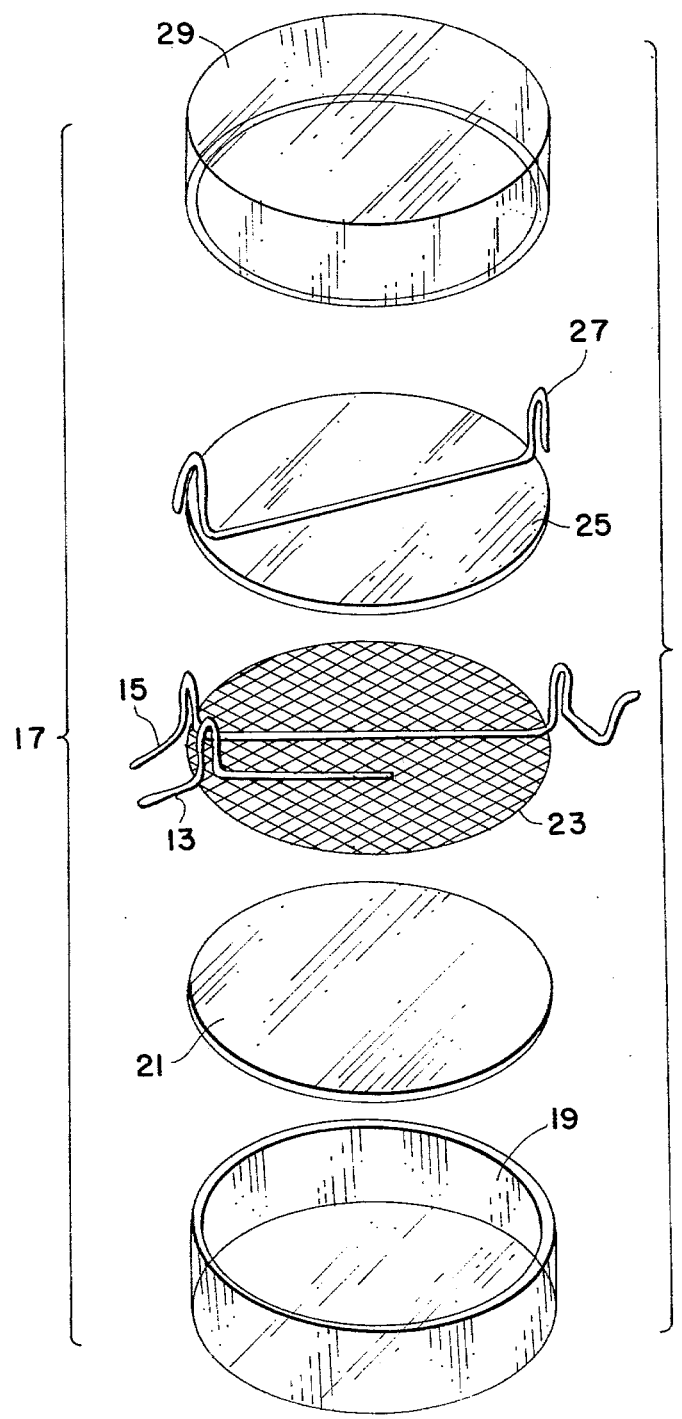
FIG. 2 is an exploded view of the container assembly of the apparatus shown in FIG. 1.

Referring now to FIG. 2, petri dish 17 includes base half 19; a bottom absorbent pad 21; membrane filter 23; electrodes 13 and 15; a top absorbent pad 25; a retainer ring 27; and, a cover half 29.

In a specific example, container 17, consisting of base half 19 and cover half 29, was a 60×15 mm petri dish acquired from Falcon, Division of Becton, Dickinson & Company, 1950 Williamsburg Drive, Oxnard, Calif. 93030; absorbent pads 21 and 25 were 47 mm diameter and acquired from Millipore Corporation, Bedford, Mass. 01730; membrane filter 23 was a 0.45 µm pore size filter GN-6, obtained from the Gelman Instrument Company, 600 South Wagner Road, Ann Arbor, Mich. 48106; and electrodes 13 and 15 were constructed from 24 gauge (0.508 mm) diameter platinum wire with a length ratio of electrode 15 to electrode 13 being approximately 2:1, i.e., 50 and 25 mm, respectively. One end of electrode 13 and both ends of electrode 15 were bent in hairpin fashion to provide a 90° bend in the electrode to extend over and frictionally engage the edge surface of base half 19 of container 17 while maintaining a length of the individual electrodes adjacent the interior bottom surface of the base half 19. Retainer ring 27 may be formed of any suitable pliable wire and in the specific example illustrated was formed of 19 gauge (0.90 mm) diameter steel wire with the end portions thereof also bent in hairpin fashion 90° to the main wire length so as to permit engagement with the electrode-membrane-pad assembly when the rim portions are frictionally clamped over the edge of the base half 19 of container 17. As shown more clearly in FIG. 1 when the container 17 is assembled with its electrode-membrane-pad assembly in place, retainer ring 27 is disposed at right angles to electrodes 13 and 15 to maintain constant pressure and close contact between pads 21 and 25, filter 23 and electrodes 13 and 15. Container 17 is sealed at the edges of cover half 29 and base half 19 as indicated by reference numeral 20 by a conventional laboratory sealant to reduce moisture loss. In the specific example described herein the sealant material 20 was Parafilm "M", a registered tradename product of the American Can Company, Marathon Products Division, Neenah, Wis.

Prior to connecting the electrodes to the strip chart recorder (Model 194, Honeywell Industrial Division, Fort Washington, Pa.), each channel was set at a zero reference point. The 25 and 50 mm electrodes were connected to the positive and negative terminals, respectively, of the recorder operated at 0.2 or 0.5 volts full scale with a chart speed of 10 min/in (24.5 mm). The electrodes were allowed to equilibrate for 60 to 80 minutes before establishing a baseline which was generally offset from the recorder zero reference point by 10 to 20 millivolts in the positive direction. Responses in the upward directon from the baseline were considered positive and downward negative. Millivolt measurements for peak height responses were made from the baseline in either the positive or negative direction. Detection time endpoints (lag time) were read from the strip chart trace and recorded as the time between challenge and the initial increase in voltage. Each trace was characterized as to the type of response curve and the maximum millivolt response was also recorded.

In operation, the time between challenge and the initial increase in voltage of an electrochemical detection system is known to be a function of the number of cells in the inoculum. For *Escherichia coli*, the detection times, for example, for $10^5$ and $10^1$ cells/ml were four and eight hours, respectively. This lag time is dictated by the requirement for a cell population of $10^6$ to $10^7$ cells/ml at the time of response. In practice, when organisms are present in very low numbers, especially in large volumes, in addition to extended lag times there is an increased probability of missing cells when samples are limited to 1, 10 or even 50 ml. To circumvent this problem, the sample is filtered through membrane filter 23 and the membrane placed between absorbent pads 21 and 25 that are moistened with a nutrient growth medium specific for the organism being tested. For *Escherichia coli*, the growth medium chosen was Trypticase soy broth (TBS, BBL, Division of Becton, Dickinson & Company, Cockeysville, Md. 21030). Absorbent pads 21 and 25 were each moistened with 2.0 ml of this broth for the tests described herein. A different nutrient medium may be employed when employing the present invention to detect and enumerate other microorganisms.

Ten milliliter volumes from a ten-fold series were filtered in dose-response studies for both *Escherichia coli* and *Staphylococcus aureus*. Bacteria were also taken from 100 ml of undiluted and $10^{-1}$ and $10^{-2}$ dilutions of estuarine and fresh water sample and collected on membrane filters. Viable counts for both the dose-response studies and the water samples were conventionally made by spreading appropriate dilutions from a ten-fold series on Trypticase soy agar (BBL) and counting colonies after 24 hour incubation at 35° C. The procedures used to determine detection time endpoints with the electrochemical apparatus of the present invention were the same as previously described in *Applied Environmental Microbiology*, Volume 36, pages 683–687, 1978.

Figure 3:
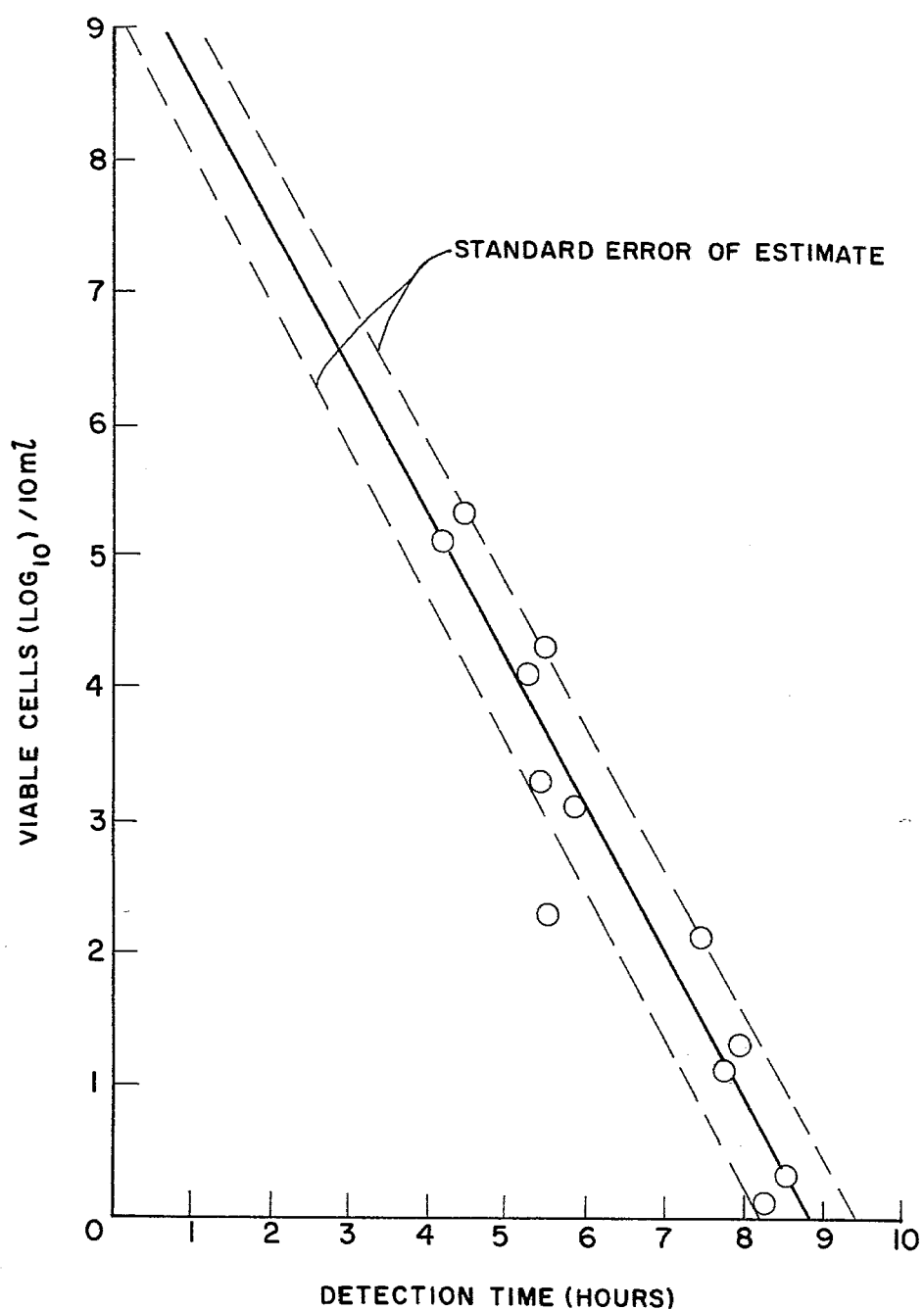
FIG. 3 is a graphic illustration of the number of specific microorganism cells (*Escherichia coli*) retained on membrane filters and detection times as obtained for a series of tests utilizing the present invention.

The dose-response curve fore *Escherichia coli* is shown in FIG. 3 and the linear regression parameters were; slope 0.0184; intercept 9.6590; and correlation coefficient 0.9508. These results compare favorably with previously published data in which platinum electrodes were tested in a broth-test tube experimental system. In the combined system of the present invention, no response, i.e., no increase in voltage was noted when *Staphylococcus aureus* was tested at the normal strip chart input resistence of 1 megohm. Responses were observed when the input resistance was increased to either $10^8$ or $10^{11}$ ohms but the endpoints were erratic and not reproducible.

Fifty estuarine and forth-six fresh water samples were tested with the present invenion and the plotted results obtained for the estuarine and fresh water samples were quite similar although slight differences were noted in the slopes, viz., 0.0101 and 0.0092 for the estuarine and fresh water samples, respectively. In monitoring water quality by relating endpoints for 100 ml samples to the curves thus obtained, these preliminary results indicate that the present invention could be employed by semi-skilled operators as an effective and rapid method for testing water purity by providing a readily obtainable estimate of the microbioal loading of different water samples.

Although the operation of the present invention has been described in connection with a specific embodiment thereof, it is not so limited and the specific structural features described herein are to be considered as illustrative only and not exhaustive.

Obviously many modifications and variations of the present invention are possible in the light of the above teachings. It is therefore to be understood that within the scope of the appended claims the invention may be practiced otherwise than as specifically claimed.

What is claimed as new and desired to be secured by Letters Patent of the United States is:

1. An electrochemical detection method for determining the presence and quantity of specific microorganisms in a sample solution comprising:

filtering the sample solution through a membrane filter impervious to the organism to be detected and quantified;

assembling a pair of electrodes in spaced adjacency relative to each other and each electrode being positioned in abutting relationship with the membrane filter;

positioning the membrane filter and electrodes between two absorbent pads adapted to fit within an open container;

positioning the absorbent pad-filter-electrode assembly within the container so as to leave at least one exposed end of each electrode extending from the container;

providing a retaining clip extending over and contacting the edges of the container and having portions thereof abutting and retaining the absorbent pad-filter-electrode assembly within the container;

sealing a cover over the container so as to leave the exposed end of each electrode extending from the container; and, attaching a strip chart recorder to the exposed ends of the electrodes to detect and record the electrical output of the electrodes as a function of the presence and quantity of the specific microorganism obtained on the filter from the sample solution.

2. The method of claim 1 wherein the container is a petri dish having a base half and a cover half, and the exposed ends of the electrodes are bent in hairpin fashion so as to extend from the interior base of the petri dish over the rim edge thereof and frictionally engage the rim edge to assist in retaining the electrodes in abutting relationship with the membrane filter.

3. The method of claim 2 wherein both electrodes are formed from platinum wire having a 2:1 relative length ratio and one electrode has both end portions bent in hairpin fashion to frictionally engage the rim edge of the petri dish.

4. The method of claim 1 wherein the microorganism being tested is *Escherichia coli* and wherein the absorbent pads are moistened with a growth medium specific therefor prior to being positioned about the membrane.

5. Apparatus for rapidly determining trace microorganism impurities in a water sample comprising:

filter means for isolating trace quantities of microorganisms from a water sample;

a pair of electrodes having a relative length ratio of approximately 2:1 and constructed from the same material;

said pair of electrodes being disposed in spaced adjacencey to each other and in contact with said filter means;

a pair of absorbent pads in contact with and forming a sandwich configuration with said electrodes and said filter means;

container means for housing the absorbent pad-filter means-electrode sandwich configuration; and means electrically connected to said electrodes to detect and enumerate microorganism isolated on said filter means.

6. The apparatus of claim 5 wherein said electrodes are formed of platinum wire and said means electrically connected to said electrodes is a strip chart recorder.

7. The apparatus of claim 6 wherein said container is a petri dish and said electrodes are provided with portions thereof frictionally engaging said petri dish to assist in maintaining said electrodes in a fixed position within said petri dish.

8. The apparatus of claim 7 including a retainer clip having ends thereof formed to frictionally engage the petri dish and having an intermediate elongated portion abutting the pad-electrode-filter sandwich assembly to assist in retaining the sandwich assembly within said petri dish, said retainer clip being disposed essentially 90° relative to said electrodes, and means sealing said petri dish so as to maintain portions of said electrodes extending from said dish.

9. The apparatus of claim 5 wherein said absorbent pads include a nutrient medium for stimulating specific microorganism growth on said filter means.

* * * * *